United States Patent
Kanel

(10) Patent No.: US 8,770,557 B2
(45) Date of Patent: Jul. 8, 2014

(54) HUMIDIFIER WITH IMPROVED HEATED SCENT MECHANISM

(75) Inventor: Christopher S. Kanel, Hudson, NY (US)

(73) Assignee: Helen of Troy Limited, St. Michael (BB)

( * ) Notice: Subject to any disclaimer, the term of this patent is extended or adjusted under 35 U.S.C. 154(b) by 304 days.

(21) Appl. No.: 13/315,638

(22) Filed: Dec. 9, 2011

(65) Prior Publication Data

US 2012/0211906 A1    Aug. 23, 2012

Related U.S. Application Data

(60) Provisional application No. 61/422,040, filed on Dec. 10, 2010.

(51) Int. Cl.
*B01F 3/04* (2006.01)
(52) U.S. Cl.
USPC . 261/142; 261/119.1; 261/128; 261/DIG. 65; 261/DIG. 88; 261/DIG. 89

(58) Field of Classification Search
USPC ............... 261/119.1, 128, 141, 142, DIG. 65, 261/DIG. 88, DIG. 89
See application file for complete search history.

(56) References Cited

U.S. PATENT DOCUMENTS

| | | | |
|---|---|---|---|
| 5,497,942 A | 3/1996 | Zingle et al. | |
| 6,196,527 B1 | 3/2001 | Huang | |
| 7,011,795 B2 | 3/2006 | Thompson et al. | |
| 7,677,536 B2 | 3/2010 | Wang et al. | |
| 7,694,675 B2 | 4/2010 | Koch et al. | |
| 2006/0131449 A1 | 6/2006 | Azukizawa et al. | |
| 2011/0221078 A1* | 9/2011 | Lev et al. | 261/81 |

* cited by examiner

*Primary Examiner* — Robert A Hopkins
(74) *Attorney, Agent, or Firm* — Stroock & Stroock & Lavan LLP

(57) ABSTRACT

A portable appliance includes a humidifier and a heated scent mechanism. The heated scent mechanism includes a scent generator that harvests excess heat produced by a liquid heating chamber, or heat produced as a byproduct of motor operation. The humidifier may be controllable such that the appliance can serve as either a humidifier or air-freshener, individually or simultaneously.

17 Claims, 6 Drawing Sheets

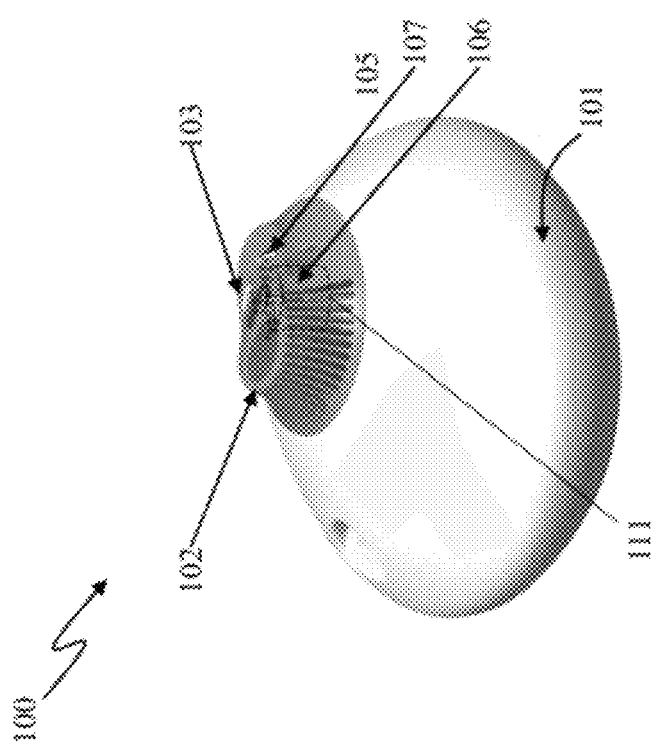
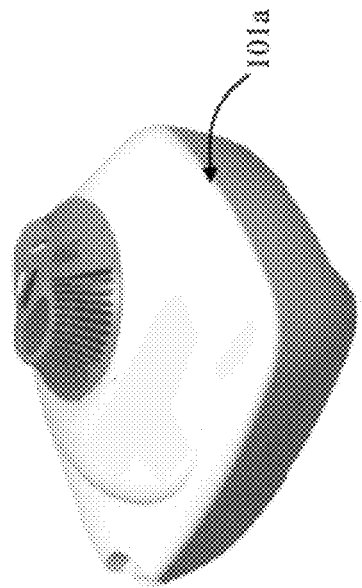
FIG. 2A
FIG. 2B

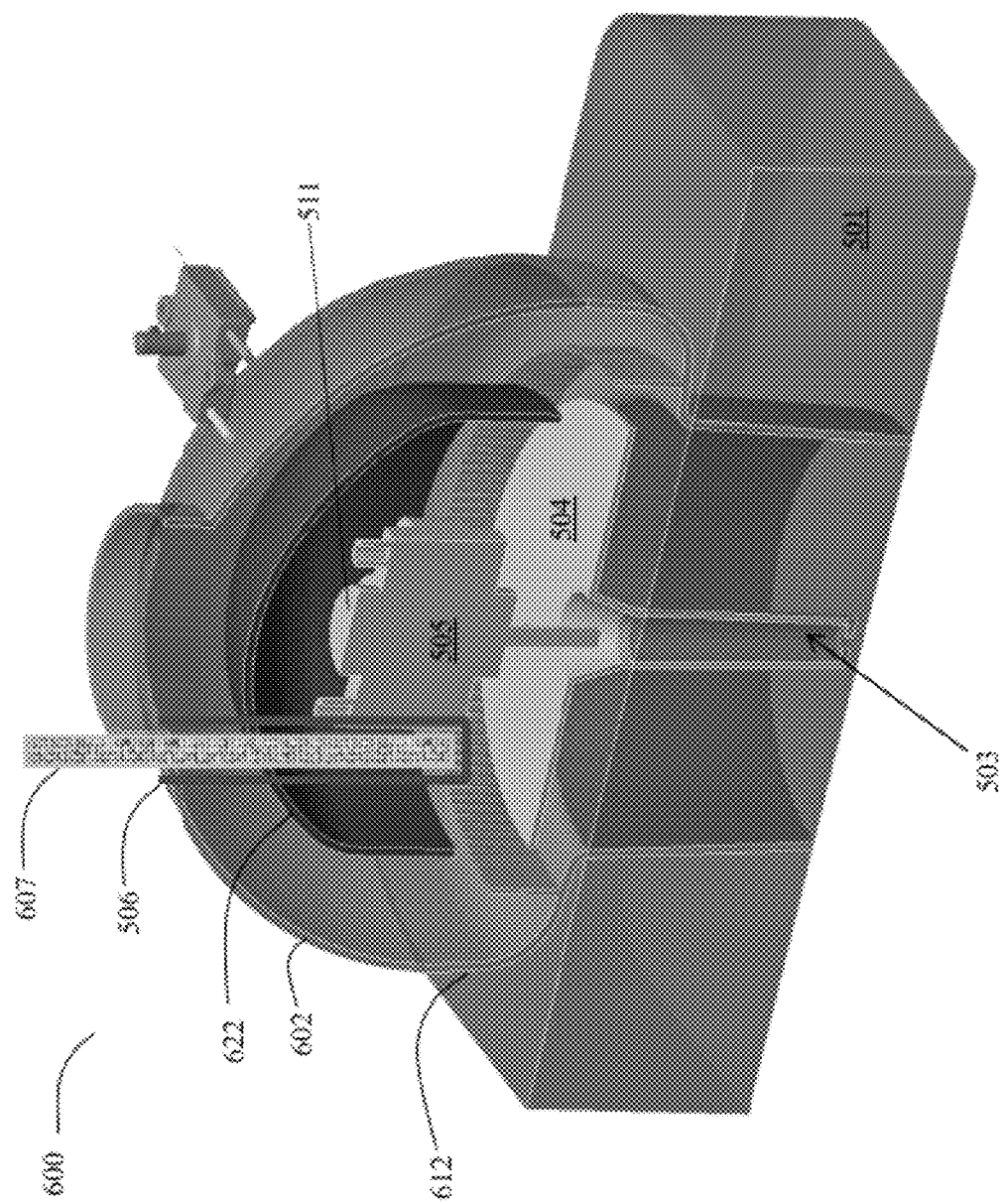

HUMIDIFIER WITH IMPROVED HEATED SCENT MECHANISM

CROSS-REFERENCE TO RELATED APPLICATIONS

This application claims the benefit of U.S. provisional patent application No. 61/422,040, filed on Dec. 10, 2010, the contents of which are incorporated herein by reference.

BACKGROUND OF THE INVENTION

1. Field of the Invention

The invention generally relates to humidifiers, and more specifically relates to humidifiers having a heated scent mechanism.

2. Description of the Related Art

The ability to easily and efficiently control indoor environments is highly desirable. For this reason, a number of devices have been developed to control the temperature, humidity, odor and air quality of enclosed environments, such as the rooms of a house. In order to control these characteristics, multiple devices are needed inside the room. This causes a problem when there are a limited number of outlets in the room. Further, the number of devices needed to control all of the desired environmental characteristics in a room can result in an unsightly mess and crowding of the room.

In temperate climates controlling humidity can be very important. During the winter and the months surrounding the winter, a lack of humidity in the air can cause significant discomfort to people. Humidifiers are a typical device used to control humidity. During these same months, many people develop colds and have sinus and chest congestion. One method for treating congestion and colds is by dispersing medicinal vapors in the air, for example menthol. The medicinal vapors help reduce cold symptoms as well as sinus and chest congestion. Medicinal vapors can be dispersed by scent generators, similar to air fresheners.

Humidifiers including means for generating a scent have been developed but have various drawbacks. These humidifiers include an air freshener to disperse an aesthetic scent into the environment. Known humidifiers having an air freshening capability include humidifiers with scented objects disposed in an air path generated by a fan of the humidifier. The scented object continuously diffuses a scent into the air and the fan blows the scent into the surrounding environment. Another known device is a vaporizing humidifier which holds a liquid scent which is heated by the vaporized water. The scent dissipates into the atmosphere as it is heated. Both of these devices, however, are limited because the humidifier and air freshener cannot act independently and the scent is dispersed by the airflow or vapor created upon activation of the humidifier. Further, the first device described above has an additional drawback in that the air-freshening mechanism continuously diffuses scent into the air. This type of air-freshener cannot be turned off or deactivated. Even without the fan, natural air currents will spread the scent throughout the room.

U.S. Pat. No. 7,677,536 to Wang et al. ("Wang"), the contents of which are incorporated herein by reference, discloses a portable appliance including a humidifier and an electrically heated scent mechanism. The heated scent mechanism includes a scent generator and an electrical heating element dedicated to heating the scent. The dedicated electrical heating element introduces extra costs, complexity and potential failure points into the design. Furthermore, in some locations, regulations may limit design options when designing a consumer product that combines a water bowl with an electrical heater.

Thus, there is a need for a combination humidifier and scent generator which allows each of the scent generating and humidifying component to operate independently, and which is simpler and less expensive than existing designs.

SUMMARY OF THE INVENTION

One embodiment of the invention includes a reservoir configured to hold water, and humidifier equipment in fluid communications with the reservoir to generate humidified air using water held in the reservoir. The humidifier equipment includes a heat source that is at least partially surrounded by an enclosure. The humidifier has a holder that is configured to hold a scent-releasing element, such as a scent pad. The holder is thermally coupled to the enclosure. In preferred embodiments of the invention the holder contacts the enclosure. In some embodiments of the invention the heat source is a heating element that heats water from the reservoir, while in other embodiments of the invention the heat source is a motor. In certain embodiments of the invention the holder is in the form of a recess having a first surface that faces a corresponding second surface of the enclosure, and the holder holds the scent pad in contact with the first surface; preferably, the first surface contacts the second surface.

Some embodiments of the invention may further provide an adjustable exposure mechanism to control exposure of the scent pad disposed within the holder.

In a specific embodiment of the invention the reservoir is provided by a first housing that has an opening, and the humidifier equipment includes a heating element. The enclosure is provided by an inner cap that is coupled to a top portion of the heating element and by a heating chamber that encloses a longitudinal length of the heating element. A second housing is coupled to the inner cap and is removably disposed over the opening of the first housing. The holder is in the form of a slot disposed in the second housing, and a surface of the slot contacts a surface of the inner cap to thermally couple the slot with heat generated from the heating element via conduction through the enclosure. The inner cap can have a thermal conductivity that exceeds the thermal conductivity of the second housing.

Another embodiment of the invention includes a method for generating a scent using heat from a humidifier. The humidifier has humidifying equipment with a heat source. Excess heat from the heat source is used to heat a scent-releasing element by positioning the scent-releasing element at a location that is in thermal communications with the heat source. In certain embodiments a slot configured to hold the scent-releasing element is utilized to position the scent-releasing element. The slot can be positioned so that the slot directly contacts an enclosure of the heat source, in which the enclosure at least partially encloses the heat source.

BRIEF DESCRIPTION OF THE DRAWINGS

The various aspects and embodiments disclosed herein will be better understood when read in conjunction with the appended drawings, wherein like reference numerals refer to like components. For the purposes of illustrating aspects of the present application, there are shown in the drawings certain preferred embodiments. It should be understood, however, that the application is not limited to the precise arrangement, structures, features, embodiments, aspects, and devices shown, and the arrangements, structures, features, embodiments, aspects and devices shown may be used singularly or in combination with other arrangements, structures, features, embodiments, aspects and devices. The drawings are not necessarily drawn to scale and are not in any way intended to limit the scope of this invention, but are merely presented to clarify illustrated embodiments of the invention. In these drawings:

FIGS. 2A, 2B are perspective views in accordance with embodiments of the invention;

FIG. 6 is a perspective cross-sectional view in accordance with an embodiment of the invention.

DETAILED DESCRIPTION OF THE PREFERRED EMBODIMENTS

Embodiments of the present invention provide a humidifier that heats a scent-releasing element. The scent-releasing element can be any object, device, substrate or the like that is used to hold and store a scent. For purposes of the following this is discussed as being a pad. It will be appreciated, however, that for the present description the term "pad" is meant to include any receptacle, substrate or device, of whatever form, that is used to hold a scent-releasing material or substance, and may include a combination of separate components, such as a receptacle that holds a scent-comprising substrate. For example, scent pads may be in the form of a solid unit or may be a liquid poured onto, into or otherwise disposed on or within a receptacle or substrate, such as a cloth substrate. The solid unit form of scent pads may be made of a gel-type air freshener held in a container, for example. Further, the scent pads may include oil or alcohol-based scent ingredients. The scent pads may have a purely aesthetic scent, such as a floral or citrus scent, or the scent may have medicinal properties. The medicinal embodiment of scent pads may include menthol, a vitamin solution, beauty lotion or other suitable substances.

The scent-releasing element (hereinafter "scent pad") is placed within the housing such that it is able to harvest excess heat generated by the one or more water heaters and/or motors, without the need for operation of a separate electrical heating element. A housing of the humidifier may be designed to place the scent pad within heat flow locations for heat produced by the motors and/or the water heater, yet also be able to accommodate parts such as a water bowl that may be available in standardized sizes with little modification to the parts. An ability to reuse standardized part sizes provides advantages such as reduced parts cost, reduced need to modify other parts that interface with the standardized parts, and reducing or eliminating changes to the cross-sectional size or footprint of the product, thereby reducing or eliminating concerns about stocking or shelving of the improved humidifiers.

Optionally, embodiments having alternate water bowl sizes may be provided as determined by market need. These embodiments may also be designed to place the scent pad within heat flow locations for heat produced by the motors and/or the water heater so as to reuse heat-affecting and/or heat-generating portions of the design, such as the motor head.

The scent pads may be placed in a location easily accessible from the outer surface of the humidifier, such that used scent pads can be easily replaced or refilled when the scent has been used up. Embodiments of the invention may also accommodate more than one scent pad, in order to provide a more intense aroma, or a composite aroma.

Figure 1:
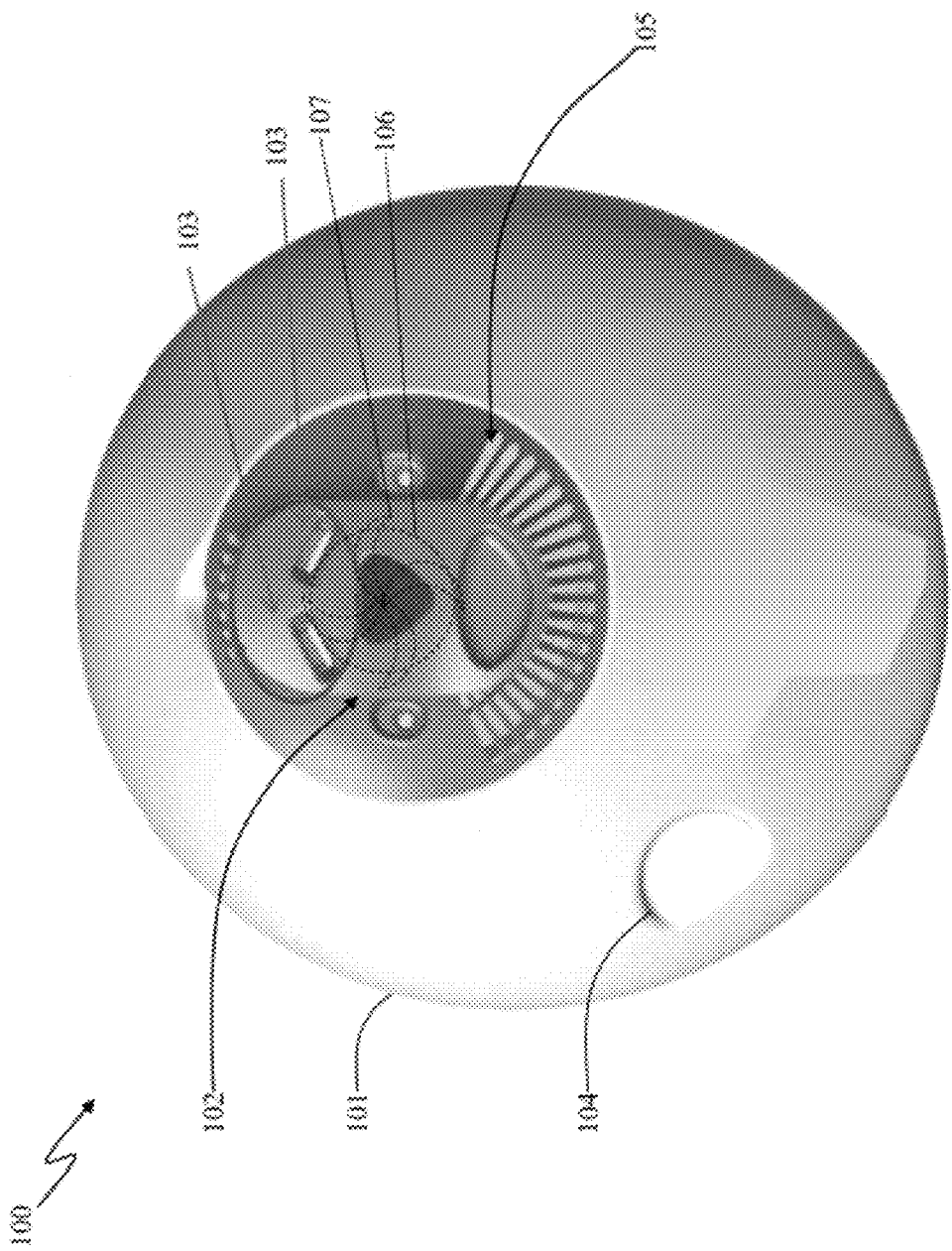
FIG. 1 is a top plan view in accordance with an embodiment of the invention.

One embodiment of the present invention is shown in FIG. 1. An overhead plan view of humidifier 100 includes a device housing provided by reservoir housing 101 and outer cap 102 removably disposed on reservoir housing 101. One or more slots 103 are provided along an outer surface of outer cap 102. Additionally, one or more ventilation openings 105 are provided along an outer surface of outer cap 102. Reservoir housing 101 may be configured as a water bowl that is used as a reservoir to hold water for evaporation during operation of the humidifier 100. In an alternate embodiment, the reservoir housing may be configured as a separate enclosure within device housing 101, 102, which may be in the form of a bag or liner, for example. Device housing 101, 102 may include one or more transparent or translucent viewports 104 used to visually determine the amount of water remaining within the reservoir 101. Device housing 101, 102 may be provided in a variety of shapes. For example, FIG. 2a is a perspective view of humidifier 100 of FIG. 1 having a curved reservoir housing 101, and FIG. 2b is a perspective view of an alternative embodiment having a more rectangular reservoir housing 101a. In operation of the humidifier 100, a flow of humidified air, generated by humidifying equipment within device housing 101, 102 and in fluid communications with the reservoir, passes through ventilation openings 105 to humidify the surrounding environment. In the case of a vaporizing humidifier, the flow may be steam.

The humidifying equipment within humidifier 100 converts water held in the reservoir 101 to moist vapor by either an evaporative mechanism (e.g., a water heater, a wick, a permanent filter, etc.), and/or an atomizing mechanism (e.g., ultrasonic, impeller disk, etc.). Either type of humidifying equipment may be provided with a motorized fan 106, 107 in order to help circulate the moist vapor. An evaporative embodiment of humidifier 100 may include a water heater as part of the humidifying equipment that is used to heat the water in or obtained from the reservoir to at least a temperature sufficient to cause vaporization, and a motor 106 that is used to circulate the moist vapor through ventilation openings 105 and into the air surrounding improved humidifier 100, such as in conjunction with fan blades 107 or the like. Another type of evaporative embodiment of humidifier 100 may include a wick that is partially immersed in water in reservoir 101. The wick draws water up from reservoir 101 by way of capillary action to a portion of the wick that is exposed to air, from which water is then evaporated. An evaporation rate can be increased by increasing an air flow over the exposed portion of the wick, e.g., by use of a fan 106, 107. Yet another type of evaporative embodiment of humidifier 100 may include as part of the humidifying equipment a permanent filter, which is known in the art as a non-wicking type of filter. The permanent filter may be constructed, for example, as an aluminum or plastic mesh. An embodiment of humidifier 100 having a permanent filter may operate by pumping water held in the reservoir up above the permanent filter and allowing the pumped water to trickle down over the permanent filter, or, alternatively, causing the filter to periodically pass through the water held in the reservoir. A fan 106, 107 can be used to increase the evaporation rate. Wick-type and permanent filter-type embodiments are operable with the water either heated or at room temperature.

Referring again to FIG. 1, and with further reference to FIG. 2A, motor 106 is covered by an exposed outer cap 102 that is disposed generally above housing 101. The motor 106 itself also includes an enclosure 111 that encloses the majority of the active components of motor 106, such as the stator and rotor, that generate heat when motor 106 operates. The enclosure 111 is thus entirely disposed within the housing 101, 102 of the humidifier 100. Heat generated by operation of motor 106 is transferred to motor enclosure 111. Motor 106, as part of the humidifying equipment within the humidifier 100, thus constitutes a source of heat. Slots 103 along an outer surface of outer cap 102 are used to hold one or more disposable scent pads and are positioned to scavenge or utilize this heat generated by motor 106. It will be appreciated that an enclosure need not fully enclose the heat generating component within the humidifier, such as motor 106; partial enclosure may be sufficient for the purposes of an embodiment of the invention. The scent pads are designed to release a scent, and release of the scent is enhanced by the heating of the scent pads. Slots 103 may be located along an upper outer surface of outer cap 102 in order to better capture by convective heat transfer the heat generated by the motor 106 and/or water heater. In other embodiments the slots 103 are configured to abut up against enclosure 111 of motor 106 so that the slots 103, or the scents pads within the slots 103, are in direct, conductive thermal contact with enclosure 111. Conductive heat transfer is less sensitive to the position of slots 103, but is more sensitive to the thermal impedances of the materials between slots 103 and heat sources such as the motor 106 and/or water heater. Use of more heat-conductive materials is preferably balanced against a need to minimize exposure of unsafe hot spots to users of the humidifier 100 and a need to minimize material and design costs.

Use of more than one slot 103, such as two slots 103, allows for use of multiple scent pads. The multiple scent pads may be configured as having the same scent, in order to provide a more intense scent, or may be configured as having different scents, in order to provide a composite scent. Scent pads may also be configured to have other differing characteristics, such as quick-acting or extended duration.

Figure 3:
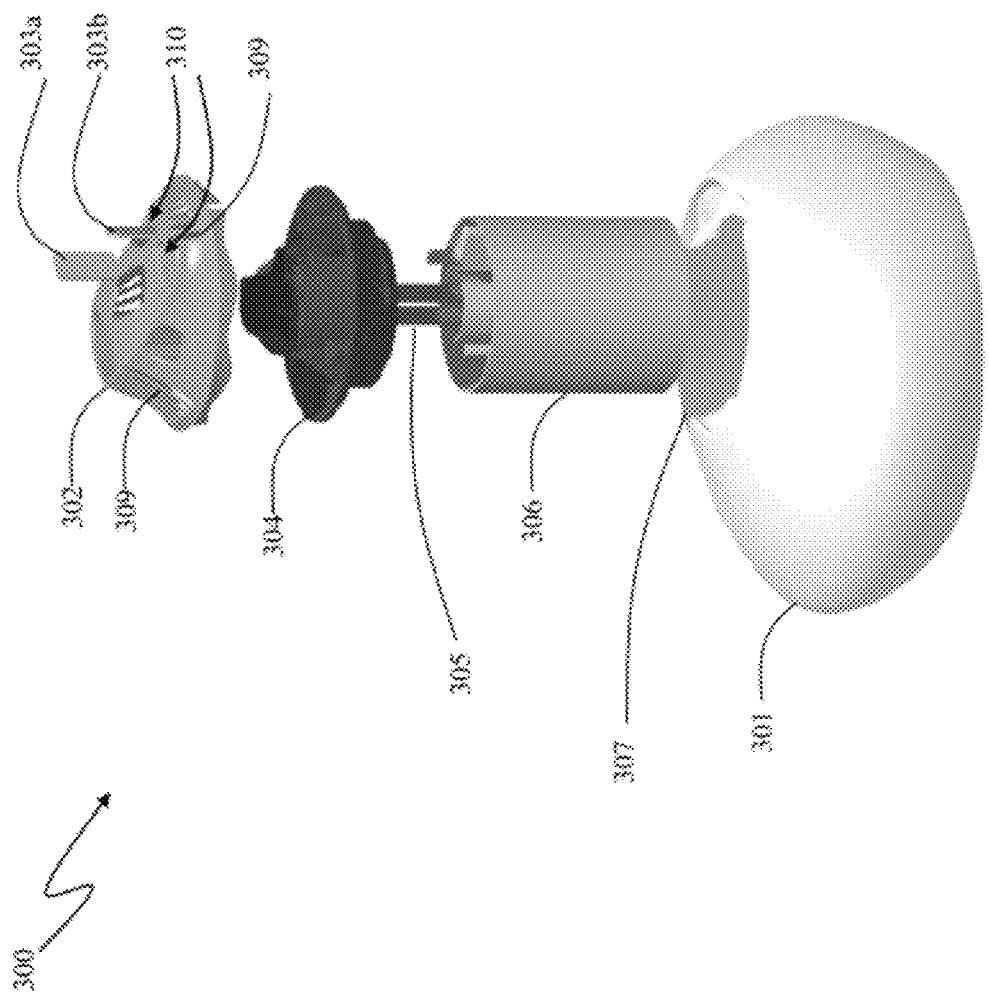
FIG. 3 is an exploded view in accordance with an embodiment of the invention.
Figure 4:
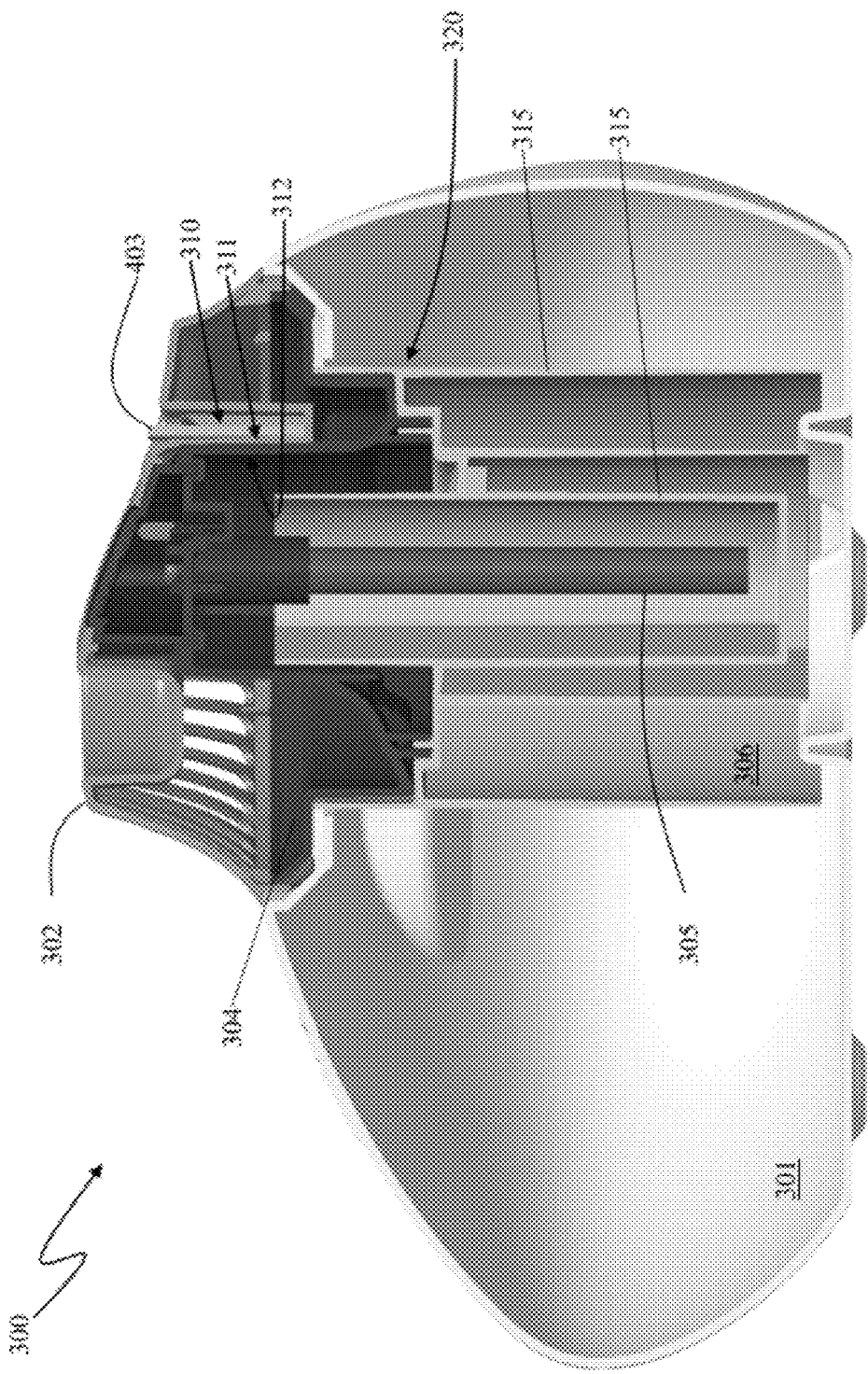
FIG. 4 is a side cutaway view in accordance with an embodiment of the invention.

FIG. 3 illustrates an exploded view of an evaporative embodiment humidifier 300 according to the present invention. Water bowl 301 serves as a water reservoir and includes along an upper surface thereof an opening 307 that is configured to accept a heating chamber 306. Heating chamber 306, having concentric walls 315, heats water within water bowl 301 by use of heat-producing elements 305 longitudinally disposed within chamber 306, and these elements 305 thus act as a heat source within the humidifying equipment of humidifier 300. The water is heated sufficiently to produce warm, moist vapors. An inner cap 304 is coupled to a top portion of the heat-producing elements 305 to cover the heat-producing elements 305, and also couples to the top portion of heating chamber 306. Referring to FIG. 4, inner cap 304 and walls 315 of heating chamber 306 serve as an enclosure 320 that encloses, but for the bottom opening of chamber 306, the heat-producing elements 305. That is, inner cap 304 covers the top portion of heating chamber 306 and heat-producing elements 305, and the heating chamber 306 covers the longitudinal lengths of heat-producing elements 305. Inner cap 304 can regulate a rate at which the moist vapor is released, such as by controlling elements 305. Inner cap 304 also helps prevent excessive heat loss from the water bowl 301 and heating chamber 306. Heat captured by the enclosure 320, and in particular inner cap 304, is conductively transferred to an outer cap 302, at least a portion of which directly contacts inner cap 304 of enclosure 320. Together, the outer cap 302 and water reservoir 301 form a device housing for humidifier 300. Inner cap 304 can be made from heat-conducting materials. Outer cap 302 is preferably not made from heat-conducting materials. Generally, inner cap 304 preferably has a thermal conductivity that is greater than the thermal conductivity of the outer cap 302. The outer cap 302 fits over inner cap 304 and includes one or more openings 309 that allow humidified air, generated by the vaporized water held in the reservoir, to be dispersed into the surrounding environment. Outer cap 302 also includes one or more slots 310 that are used to hold one or more scent pads 303a, 303b. Scent pad 303a is illustrated prior to insertion into slot 310, and scent pad 303b is illustrated in a partially inserted position in slot 310. Scent pads 303a, 303b are inserted into slots 310 sufficiently to be held securely, while having sufficient exposed surface area to allow scent to disperse and to allow used scent pads 303 to be removed. The slots 310 are positioned and configured to utilize heat generated by the elements 305. In preferred embodiments of the invention, as set forth in more detail below, this may be by way of conduction via enclosure 320; convectional approaches are also possible, however.

FIG. 4 illustrates an assembled cross-sectional view of embodiment 300 of the present invention. Heating chamber 306 is disposed within water bowl 301, and thus is fluidly coupled to the water held in the water reservoir provided by bowl 301. Heating element 305 is disposed within heating chamber 306, and thus is surrounded and partially enclosed by enclosure 320. This enclosure, in turn, is entirely disposed within the device housing 301, 302. Above heating chamber 306 is the inner cap 304 of the enclosure 320, above which is disposed the outer cap 302 of the device housing. Slots 310 of outer cap 302 are formed and positioned such that when outer cap 302 is assembled with inner cap 304, the scent pads 303a, 303b are held close to inner cap 304 in order to promote heat conduction. Scent pad 403 is illustrated in an inserted position in outer cap 302. Scent pad 403 is located within a heat flow path from heater 305 in order to harvest heat for heating scent pad 403. Preferably, the slot 310 is formed as a recess within outer cap 302 of the device housing, and a majority of the surface area of the scent pad 403 is aligned flush and in contact with a corresponding heated surface 311 of the slot 310. Heated surface 311 of slot 310 is, in turn, in contact with a corresponding surface 312 of enclosure 320, provided by inner cap 304, so that heat is conductively transferred from the enclosure 320 to the scent pad 403 via the heated surface 311 of slot 310. The slot 310 is thus preferably configured so as to present a surface area 311 that abuts a sufficiently large portion 312 of the enclosure 320. Clamps, grooves, or the like within slot 310 can be used to hold scent pad 403 against heated surface 311; or, slot 310 can be configured to be sufficiently narrow such that scent pad 403 frictionally engages with heated surface 311.

Figure 5:
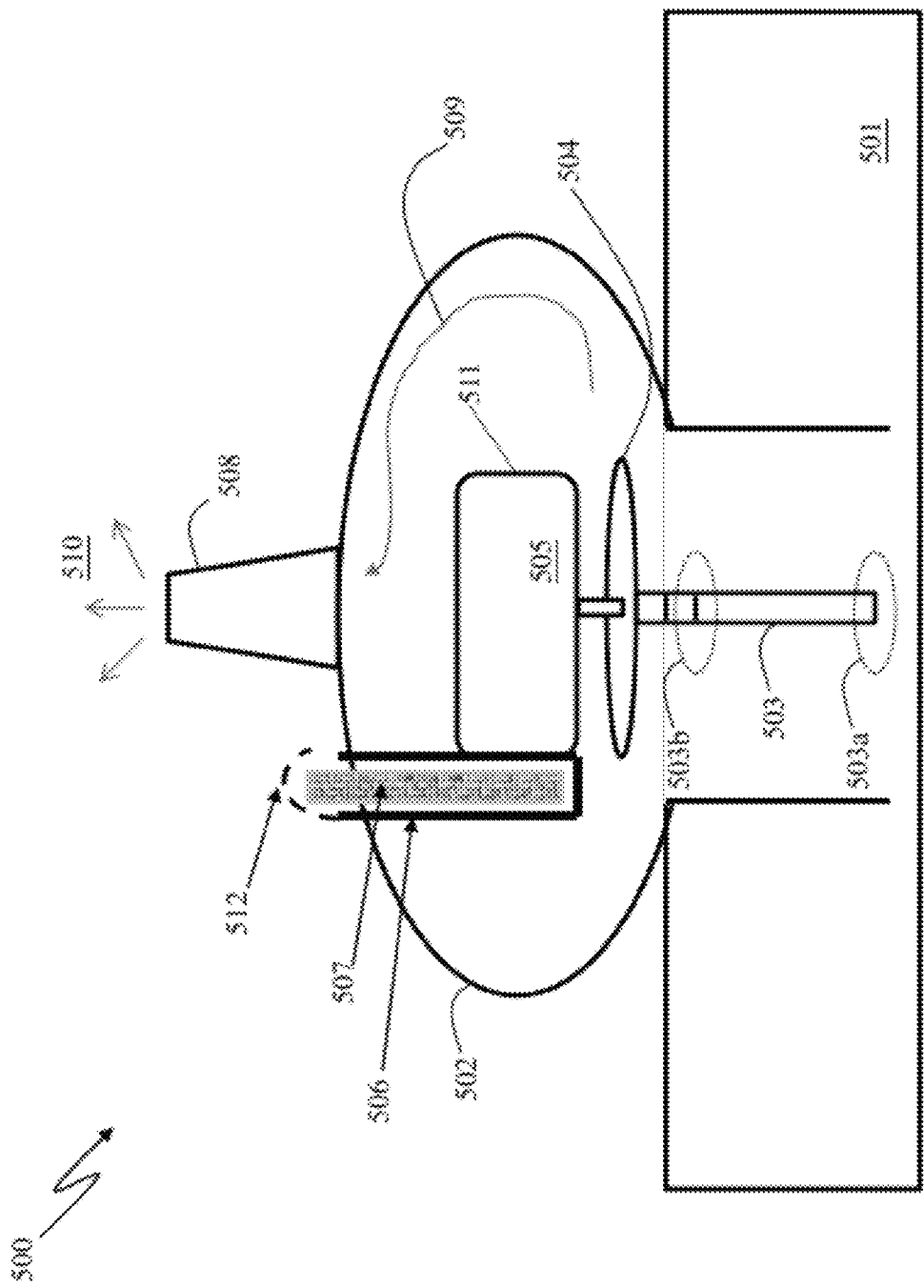
FIG. 5 is a schematic view in accordance with an embodiment of the invention.

FIG. 5 illustrates a schematic view of an atomizing embodiment 500 of the present invention. A water bowl 501 serves as a water reservoir and has an aperture along an upper surface of water bowl 501 that is removably coupled to a top housing 502 at the aperture of water bowl 501. The water bowl 501 and top housing 502 together serve as a device housing for humidifier 500. Optionally, a water heater in thermal contact with water within water bowl 501 may also be provided. Top housing 502 encloses a pick-up tube 503 having two ends 503a and 503b. End 503a extends into water bowl 501, near the bottom, in order to pick up water within the reservoir. End 503b of pick-up tube 503 is coupled to an impeller disk 504 that is outside of water bowl 501 but inside housing 502. Impeller disk 504 is configured to convert liquid water drawn through pick-up tube 503 into a mist or gaseous form or the like, referred to herein generically as "mist." For instance, impeller disk 504 may be a sputtering device, an ultrasonic device, etc., or a combination thereof. A motor 505 inside device housing 501, 502 is positioned near impeller disk 504, for instance above impeller disk 504, and drives impeller disk 504. Motor 505 itself includes an enclosure 511 that encloses the active, heat-generating components of motor 505. Coupled in direct thermal contact with enclosure 511 of motor 505 is scent pad holder 506, which is configured to contain scent pad 507. Scent pad 507 is infused with a releasable scent. Scent pad holder 506 is physically accessible from outside of embodiment 500 and is configured to allow at least a portion of scent pad 507 to be exposed to air surrounding embodiment 500. Housing 502 includes one or more openings 508. Optionally, motor 505, pick-up tube 503 and/or impeller disk 504 may be removable from housing 502.

Operation of embodiment 500 begins by first removing top housing 502 from water bowl 501 and filling water bowl 501 sufficiently to a level that will immerse end 503a of pick-up tube 503 when embodiment 500 is in an assembled position. Top housing 502 is then reattached to water bowl 501 and the embodiment 500 is turned on by energizing motor 505. Water is drawn up pick-up tube 503 to impeller disk 504, e.g., by wicking, capillary action, by a pump powered by motor 505, or by any other suitable means. Water so drawn up is converted into a mist 509 by impeller disk 504, and the mist 509 is circulated within housing 502 by convection, the action of motor 505 rotating a fan, or by any other suitable means. Circulated mist 509 flows toward and through openings 508 and is released as humidified air 510. Fan speed can be controlled in order to adjust the rate at which humidified air 510 is released. Hence, motor 505 can be electrically coupled to suitable control electronics, as known in the art, which accept input from the user via a user interface, such as knobs, buttons or the like, to control the operating rate of the device 500.

Motor 505 generates heat as a byproduct of its operation, which is transferred to enclosure 511. At least a portion of the heat generated by motor 505 is conducted to at least one scent pad holder 506 and thereon conducted, convected or both to scent pad 507, increasing the temperature of scent pad 507. Scent pad 507 so warmed releases its infused scent at a faster release rate, thereby offering benefits such as more quickly changing scent in a space surrounding embodiment 500, or providing a more intense scent in the space, etc. Scent pad 507 has a useful lifetime which ends when the infused scent is substantially released. Scent pad 507 can be provided in a variety of sizes and shapes (e.g., lengths, T-shape, etc.) to provide various lifetimes, release rates, or portions having distinct scents.

An efficiency of the heat transfer from scent pad holder 506 to scent pad 507 can be controlled. One method of controlling this efficiency is by adjusting the depth of insertion of scent pad 507 into scent pad holder 506. An efficiency of scent release can be controlled by providing an adjustable exposure mechanism 512. The adjustable exposure mechanism may be by way of louvers, slidable covering over an opening, or other variable-sized opening, provided on the body of scent pad 507 or, as shown in FIG. 5, on scent pad holder 506 itself. The adjustable opening 512 controls the exposure of scent pad 507 to the draft of passing air. Overall efficiency is a function of both the efficiency of heat transfer and the efficiency of scent release. A controllable overall efficiency can allow a user to trade off lifetime of scent pad 507 with intensity of scent, for instance a short lifetime for intense scent, or longer lifetime for a less intense scent.

FIG. 6 illustrates an assembled, cross-sectional, perspective view of embodiment 600 of the present invention. Several aspects of embodiment 600 are similar to aspects of embodiment 500. The top housing of embodiment 600 is illustrated as an upper housing 602 coupled to a lower housing 612. Upper housing 602 and lower housing 612 may have different thermal conductivities, which may be useful for conducting heat from optionally heated water within water bowl 501 to scent pad holder 506 and scent pad 507 through lower housing 612, yet discouraging unwanted heat loss through upper housing 602. Hence, lower housing 612 may be thermally conductive while upper housing 602 is thermally insulative. An additional inner housing 622 may be provided to help regulate the amount of moist vapor released and/or prevent excessive water loss. Excess water may collect on the inner surface of inner housing 622, and eventually drip or flow back into the reservoir of water bowl 501. Embodiment 600 also illustrates scent pad 607 having a greater portion exposed from scent pad holder 506, compared to the combination of scent pad holder 506 and scent pad 507 illustrated in embodiment 500.

Embodiments of the humidifier described herein can be sized for domestic use and made portable such that they can be easily moved from room to room. Embodiments of the humidifier may include an electrical cord and plug which draw current from an outlet for the operation of the humidifying equipment within the humidifier. A control panel may be disposed on the housing and may include user controls, such as buttons, switches, dials or the like, for controlling embodiments of the humidifier.

Those skilled in the art will recognize that the present invention has many applications, may be implemented in various manners and, as such is not to be limited by the foregoing embodiments and examples. Any number of the features of the different embodiments described herein may be combined into a single embodiment, the locations of particular elements can be altered and alternate embodiments having fewer than or more than all of the features herein described are possible. Functionality may also be, in whole or in part, distributed among multiple components, in manners now known or to become known.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention. While there has been shown and described fundamental features of the invention as applied to being exemplary embodiments thereof, it will be understood that omissions and substitutions and changes in the form and details of the disclosed invention may be made by those skilled in the art without departing from the spirit of the invention. Moreover, the scope of the present invention covers conventionally known, future developed variations and modifications to the components described herein as would be understood by those skilled in the art. It is the intention, therefore, to be limited only as indicated by the scope of the claims appended hereto.

What is claimed is:
1. A humidifier comprising:
a reservoir configured to hold water;
humidifier equipment in fluid communications with the reservoir to generate humidified air using water held in the reservoir, the humidifier equipment comprising a heat source;

an enclosure at least partially enclosing the heat source; and a holder configured to hold a scent-releasing element, the holder thermally coupled to the enclosure.

2. The humidifier of claim 1 wherein the holder contacts the enclosure.

3. The humidifier of claim 1 wherein the heat source is a heating element configured to heat water from the reservoir.

4. The humidifier of claim 1 wherein the heat source is a motor.

5. The humidifier of claim 1 wherein the holder comprises a first surface that faces a corresponding second surface of the enclosure, and the holder is configured to hold the scent-releasing element in contact with the first surface.

6. The humidifier of claim 5 wherein the first surface contacts the second surface.

7. The humidifier of claim 1 further comprising an adjustable exposure mechanism to control exposure of the scent-releasing element disposed within the holder.

8. The humidifier of claim 1 wherein the reservoir is provided by a first housing, the first housing having an opening, the humidifier equipment comprises a heating element, and the enclosure comprises an inner cap coupled to a top portion of the heating element and to a heating chamber enclosing a longitudinal length of the heating element, the humidifier further comprising a second housing coupled to the inner cap and configured to be removably disposed over the opening of the first housing, wherein the holder includes a slot disposed in the second housing, and a surface of the slot contacts a surface of the inner cap to thermally couple the slot with heat generated from the heating element via conduction through the enclosure.

9. The humidifier of claim 8 wherein the inner cap has a thermal conductivity that exceeds a thermal conductivity of the second housing.

10. A method for generating a scent using heat from a humidifier, the humidifier comprising humidifying equipment having a heat source, wherein the humidifying equipment is in fluid communication with a reservoir configured to generate humidified air using the water held in said reservoir, the method comprising:

utilizing heat from the heat source to heat a scent-releasing element by positioning the scent-releasing element at a location that is in thermal communication with the heat source.

11. The method of claim 10 further comprising utilizing a slot configured to hold the scent-releasing element.

12. The method of claim 11 further comprising positioning the slot so that the slot directly contacts an enclosure of the heat source, the enclosure at least partially enclosing the heat source.

13. A holder for a scent-releasing element of a humidifier, the scent holder comprising:

a slot comprising a first surface and configured to removably hold a scent-releasing element in contact with the first surface, wherein the slot is further configured for placement in the humidifier so that the first surface contacts an enclosure of a heat source in the humidifier;

an adjustable exposure mechanism for adjustably controlling exposure of the scent-releasing element.

14. The holder of claim 13 wherein the holder comprises a plurality of slots configured to removably hold a corresponding plurality of scent-releasing elements.

15. A humidifier comprising:

a reservoir configured to hold water;

humidifier equipment in fluid communication with the reservoir to generate humidified air using water held in the reservoir; and a holder configured to hold a scent-releasing element, the holder having a slot comprising a first surface and configured to removably hold a scent-releasing element in contact with the first surface, wherein the slot is further configured for placement in the humidifier so that the first surface contacts an enclosure of a heat source in the humidifier.

16. The humidifier of claim 15 further comprising an adjustable exposure mechanism to control exposure of the scent-releasing element disposed within the holder.

17. The humidifier of claim 15 wherein the heat source is a motor.

* * * * *